United States Patent [19]

Ishiguro et al.

[11] Patent Number: 5,257,628
[45] Date of Patent: Nov. 2, 1993

[54] ULTRASOUND INTERNAL EXAMINATION SYSTEM

[75] Inventors: Masaaki Ishiguro; Toshizumi Tanaka, both of Omiya, Japan

[73] Assignee: Fuji Photo Optical Co., Ltd., Omiya, Japan

[21] Appl. No.: 910,508

[22] Filed: Jul. 8, 1992

[30] Foreign Application Priority Data

Jul. 11, 1991 [JP] Japan ................... 3-196120
Jul. 11, 1991 [JP] Japan ................... 3-196121
Jul. 11, 1991 [JP] Japan ................... 3-196123

[51] Int. Cl.$^5$ ............................................. A61B 8/12
[52] U.S. Cl. ........................ 128/662.06; 128/660.09; 128/660.04
[58] Field of Search ............ 128/660.01, 660.04, 128/662.03, 662.05, 662.06, 660.09

[56] References Cited

U.S. PATENT DOCUMENTS

| | | | |
|---|---|---|---|
| 5,050,610 | 9/1991 | Oaks et al. | 128/662.03 |
| 5,099,850 | 3/1992 | Matsui et al. | 128/662.06 |
| 5,107,844 | 4/1992 | Kami et al. | 128/660.10 |
| 5,131,393 | 7/1992 | Ishiguro et al. | 128/662.06 |

Primary Examiner—William E. Kamm
Assistant Examiner—George Manuel
Attorney, Agent, or Firm—Oblon, Spivak, McClelland, Maier & Neustadt

[57] ABSTRACT

Described herein is an ultrasound internal examination system which essentially includes an ultrasound probe having a rotatable ultrasound transducer element mounted at the tip end of a flexible cable for movement in radial and linear directions, an operating unit having remote control means for the ultrasound transducer element, including a rotating means, a linearly reciprocating means, a rotational angle sensor means, and a linear position sensor means, and a signal processing means adapted to produce at least an ultrasound tomographic image of radial scan direction or an ultrasound tomographic image of linear scan direction on the basis of ultrasound echo signals from the ultrasound transducer element and signals from the rotational angle sensor means and the linear position sensor means, and arranged to display at least one of the ultrasound tomographic images of radial and linear scan directions along with a marker indicating the linear position or angular direction of the ultrasound transducer element in the other scan direction.

5 Claims, 12 Drawing Sheets

ULTRASOUND INTERNAL EXAMINATION SYSTEM

BACKGROUND OF THE INVENTION

1. Field of the Art

This invention relates to an ultrasound internal examination system having an ultrasound probe to be endoscopically inserted into an intracavitary portion of human body or the like for ultrasound examination.

2. Prior Art

Generally, ultrasound internal examination systems are largely constituted by an ultrasound probe with an ultrasound transducer element for transmission and reception of ultrasound signals, a signal processor which has the function of controlling the transmission and reception of the ultrasound signals in addition to the function of processing received echo signals, and a monitor for displaying ultrasound images. There has been known in the art the so-called insert type ultrasound probe which is designed to be introduced into an intracavitary portion of interest, directly or through a guide means such as an endoscope or the like, and to transmit ultrasound pulses into tissues of an intracavitary portion or wall while receiving reflected echo signals. In this connection, the scan modes of ultrasound examination systems includes the so-called B mode scan in which ultrasound pulses are transmitted into an intracavitary wall portion at predetermined time intervals from an ultrasound transducer which is being moved over a predetermined scan range, and, on the basis of return echoes, an ultrasound image of the scan range is displayed on a monitor screen. For this scan mode of the ultrasound transducer, either a mechanical scan system or an electronic scan system is usually employed.

An insert type ultrasound probe of an extremely small diameter, which is intended to be inserted through a biopsy channel of an endoscope like forceps, is known, for example, from U.S. Pat. No. 4,802,487. In the ultrasound probe of this sort, there have been strong demands for further reductions in diameter and length of rigid portions on the probe, and therefore there has been no choice but to employ a single-element ultrasound transducer of small size, instead of an arrangement involving a large number of transducers as in the electronic scan system. It follows that the ultrasound probe of this type is necessarily arranged to operate with a mechanical scan system. With regard to its scanning direction, it can be put in a radial scan in which the ultrasound transducer is turned about an axis or in a linear scan in which the ultrasound transducer is moved linearly. In case of the radial scan, the scan range may extend to 360° or may be restricted to an arc of a predetermined angle.

The ultrasound examination system is usually resorted to in checking for the existence of a tumor or other diseased portion which normally has a certain degree of three-dimensional spreading, so that it is important to grasp the condition of an affected portion three-dimensionally before giving any diagnosis. However, a single-element ultrasound transducer can give only one tomographic ultrasound image in one direction of an intracavitary portion no matter whether it is in radial scan or in linear scan. To overcome this problem, attempts have been made to get a three-dimensional image of a diseased portion from a plural number of tomographic images which are taken through an ultrasound transducer at a number of different positions. For example, in a radial scanning operation, ultrasound tomographic images are sequentially taken while moving an ultrasound transducer gradually in the linear direction. However, it has been found extremely difficult to take ultrasound tomographic images accurately at uniformly spaced positions even with meticulous skills, failing to recognize the shape or other conditions of a diseased portion by way of a three-dimensional image which correctly reflects the actual condition of the disease if any.

SUMMARY OF THE INVENTION

With the foregoing situations in view, it is an object of the present invention to provide an ultrasound internal examination system which can produce ultrasound images in such a way as to permit three-dimensional examination of a diseased portion or the like by the use of simple means.

In accordance with the present invention, for achieving the above-stated objective, there is provided an ultrasound internal examination system which essentially includes: an ultrasound probe having a rotatable ultrasound transducer element mounted at the tip end of a flexible cable for movement in radial and linear directions; an operating unit having remote control means for the ultrasound transducer element, including a rotating means, a linearly reciprocating means, a rotational angle sensor means, and a linear position sensor means; and a signal processing means adapted to produce at least an ultrasound tomographic image of radial scan direction or an ultrasound tomographic image of linear scan direction on the basis of ultrasound echo signals from the ultrasound transducer element and signals from the rotational angle sensor means and the linear position sensor means, and arranged to display at least one of ultrasound tomographic images of radial and linear scan directions along with an indicator giving a sign of the position or angular direction of the ultrasound transducer element in the other scan direction.

The above and other objects, features and advantages of the invention will become apparent from the following description and the appended claims, taken in conjunction with the accompanying drawings which shows by way of example some preferred embodiments of the invention. Needless to say, the particular forms shown in the drawings are given for the purpose of illustration only and should not be construed as being limitative of the invention in any way whatsoever.

DESCRIPTION OF PREFERRED EMBODIMENTS

Hereafter, the invention is described more particularly by way of its preferred embodiments with reference to the drawings.

Figure 1:
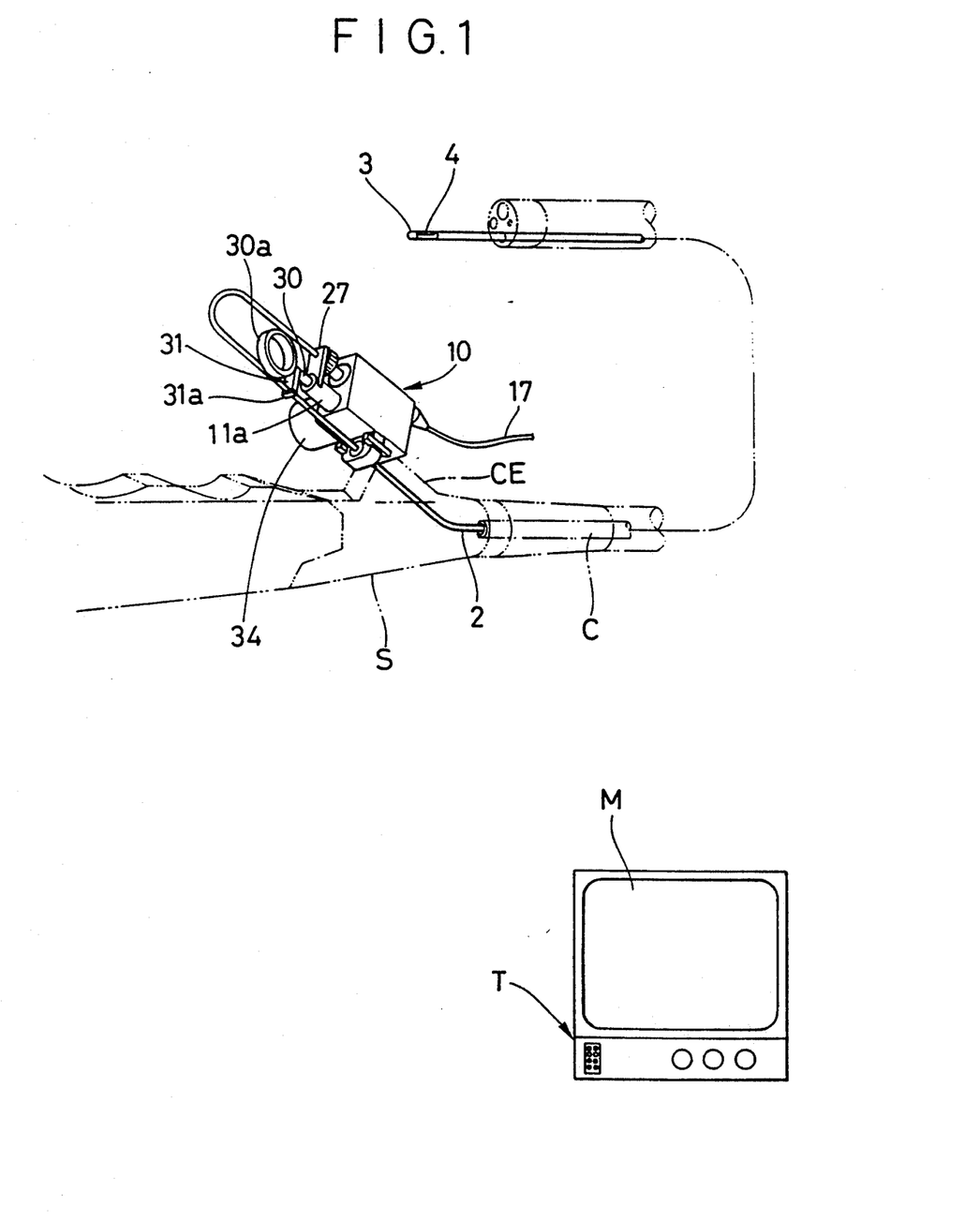
FIG. 1 is a schematic view of an ultrasound examination system in a first embodiment of the invention, showing its general arrangement.

Referring to FIGS. 1 through 6, there is shown an ultrasound internal examination system in a first embodiment of the invention, employing an ultrasound probe to be inserted through a biopsy channel C which is provided on an endoscope S for insertion of instruments like forceps. FIG. 1 shows the general arrangement of the ultrasound examination system, where indicated at 1 is an ultrasound probe having a rigid portion 3 at the tip end of a flexible cable 2 of resilient material and having a single-element ultrasound transducer 4 mounted on the rigid tip end portion 3 which is rotatable relative to the flexible cable 2. The ultrasound transducer element 4 has its active face 4a disposed in an opening which is formed at one side of the rigid tip end portion 3 for transmission and reception of signals therethrough.

Figure 2:
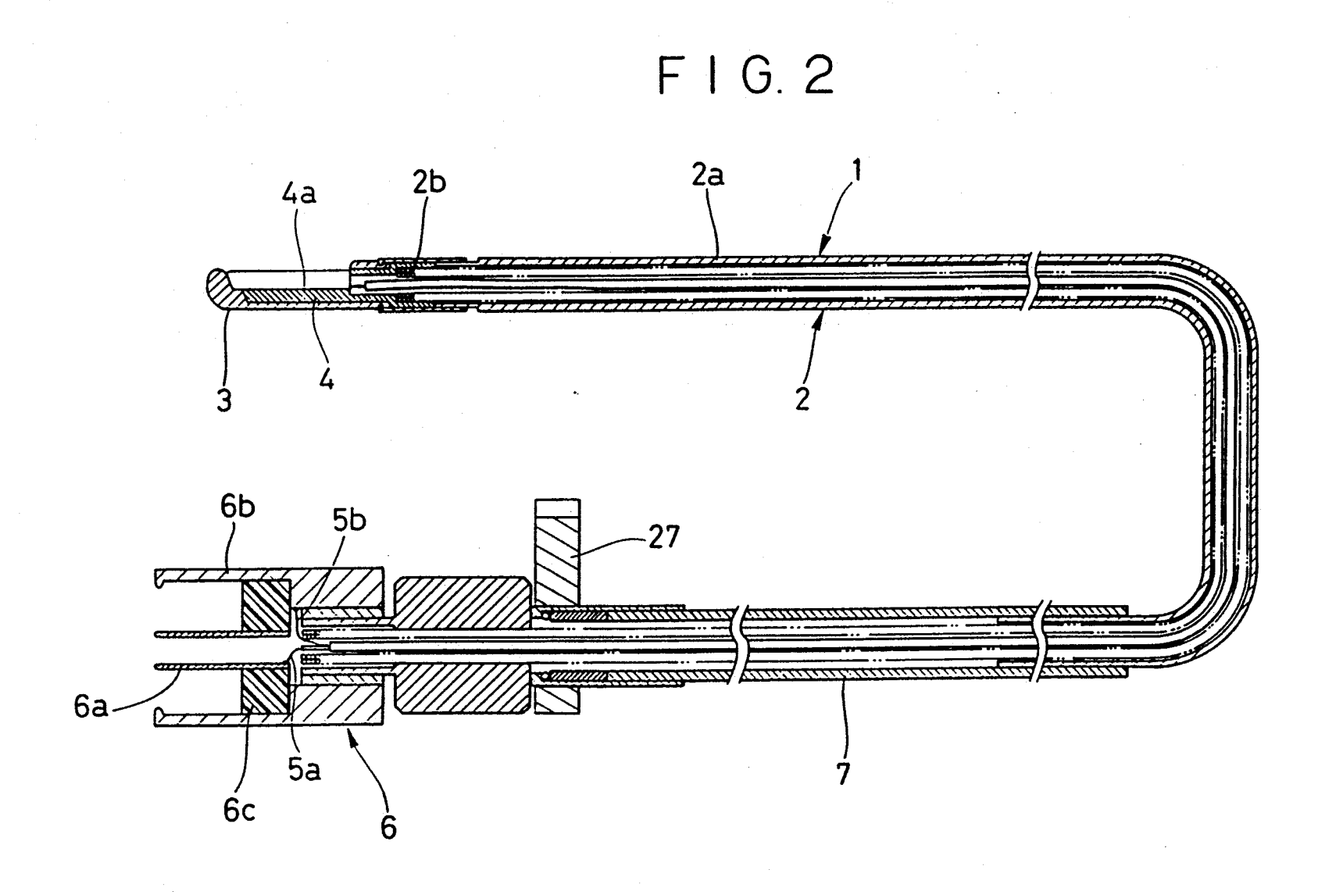
FIG. 2 is a longitudinal sectional view of an ultrasound probe.

The flexible cable 2, which is to be inserted through a biopsy channel C of the endoscope S and which also serves as a control cable, is formed in a diameter small enough for insertion into the biopsy channel C and, as shown in FIG. 2, has, within a flexible sleeve 2a of a soft friction-free material like fluorine resin, a rotation transmitting member 2b in the form of coil springs which are fitted in the sleeve 2a in superposed or parallel relation with each other. Accordingly, the flexible cable 2 has a function of rotationally driving the ultrasound transducer element 4 on the rigid tip end portion 3 through remote control. Further, a signal transmission/reception line 5 which is in the form of a coaxial cable is passed through the rotation transmitting member 2b in the flexible cable 2. The fore end of the rotation transmitting member 2b is fixedly connected to the rigid tip end portion 3 to transmit thereto the momentum of the rotating efforts for the ultrasound transducer element 4. When the ultrasound transducer element 4 is put in rotation, the signal line 5 is also rotated integrally with the rotation transmitting member 2b to prevent twisting of the line.

The ultrasound probe 1 is provided with a connector 6 at its proximal end for detachably coupling the probe 1 with the operating unit 10. The connector 6 is constituted by an electrode pin 6a and a cylindrical split socket 6b to which the proximal end of the rotation transmitting member 2b is fixedly connected. A wire 5a of the signal line 5 is connected to the electrode pin 6a, while another wire 5b of the signal line 5 is connected to the split socket 6b. This split socket 6b is formed of a conductive material and separated from the electrode pin 6a by an interposed insulating member 6c. A protective sleeve 7 of a more rigid material than that of the sleeve 2a of the flexible cable 2 is fitted on the latter over a certain length which is led out of the biopsy channel C of the endoscope S.

Figure 3:
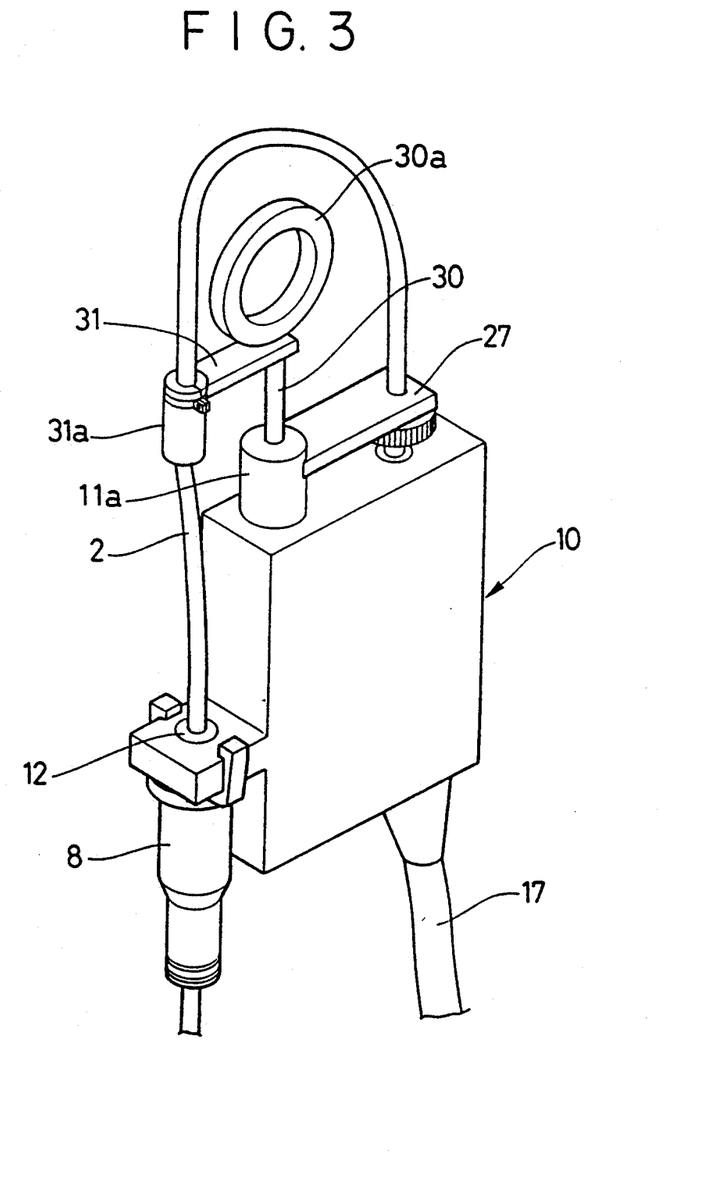
FIG. 3 is a schematic outer view of an operating unit operatively mounted on an endoscope.
Figure 4:
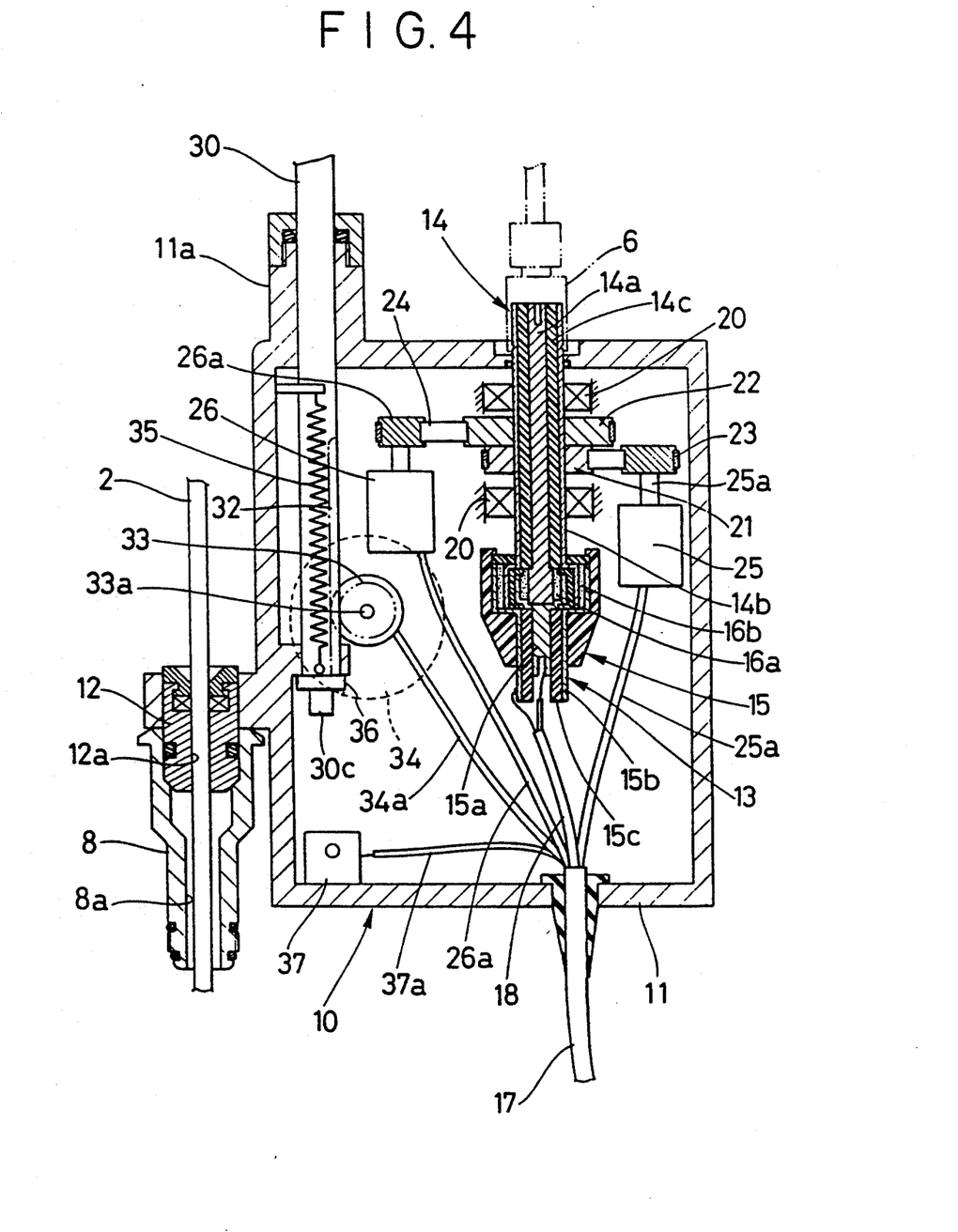
FIG. 4 is a schematic sectional view of the operating unit.

The operating unit 10 is detachably fixable on the entrance opening CE of the biopsy channel C of the endoscope S, and is arranged as shown in FIGS. 3 and 4. More specifically, the operating unit 10 is provided with a mount portion 12 on its casing 11, the mount portion 12 being provided with a mount piece 8 for coupling and uncoupling engagement with the entrance opening CE of the biopsy channel C of the endoscope S. In this instance, the mount piece 8 has a function as an adaptor which permits to mount the operating unit 10 on endoscopes of different types. The mount piece 8 and mount portion 12 are formed with holes 8a and 12a, respectively, for threading therethrough the flexible cable 2 of the ultrasound probe 1.

The connector 6 at the proximal end of the flexible cable 2 of the ultrasound probe 1, which has been led out through the holes 8a and 12a in the mount piece 8 and mount portion 12, is detachably coupled with a connector 13 on the casing 11 of the operating unit 10. The connector 13 is constituted by a rotary member 14 and a rotary connector 15. For fitting engagement with the connector 6 of the flexible cable 2, one end of the rotary member 14 is slightly protruded on the outer side of the casing 11. The rotary member 14 has functions as a rotational shaft which rotationally drives the ultrasound transducer element 4, in addition to functions as a signal transmitting member. More particularly, the rotary member 14 includes a core portion 14a which functions as one terminal to be connected to the electrode pin 6a of the connector 6, and an outer sleeve 14b which functions as the other terminal to be connected to the coupling socket 6b. An insulation layer 14c is interposed between the core portion 14a and outer sleeve 14b of the rotary member 14. The rotary member 14 has a rigid rod-like shape as a whole. The rotary connector 15 is coupled with the rotary member 14 rotatably relative to each other, and provided with an electrode 15a, which is electrically connected to the core portion 14a of the rotary member 14 through a fluid contact 17a consisting of a conductive fluid like mercury, and an electrode 15b which is electrically connected to the outer sleeve 14b through a fluid contact 17b. An insulating member 16 is interposed between the two electrodes 15a and 15b. Accordingly, through the above-described connector 6, rotary member 14 and rotary connector 15, the signal transfer line 5 which is rotatable with the ultrasound transducer element 4 is connected to a transfer line 19 in an unrotatable cable 18 which is connected to the ultrasound image observation terminal T.

Thus, the ultrasound probe 1 can be operated to make a radial scan in which the ultrasound transducer element 4 is turned in the radial direction, and a linear scan in which the transducer element 4 is moved linearly along the rigid tip portion.

The ultrasound transducer element 4 is associated with a radial scan mechanism which is arranged in the manner as follows. The rotary member 14 is rotatably supported by bearings 20 at the opposite ends thereof. A pair of pulleys 21 and 22 are mounted side by side on the rotary member 14 between the bearings 20. These pulleys 21 and 22 are connected to output shaft 25a of a rotational drive motor 25 and input shaft 26a of an encoder 26 through belts 23 and 24, respectively. Wires 25b and 26b from the motor 25 and encoder 26 are passed through the cable 18 which is connected to the ultrasound image observation terminal T. Therefore, as the motor 25 is actuated to rotate the rotary member 14, its rotation is transmitted to the coupling socket 6b of the connector 6 and then to the rotation transmitting member 2b to rotate the ultrasound transducer element 4 which is fixed to the fore end of the rotation transmitting member 2b. Simultaneously with this rotation of the ultrasound transducer element 4, ultrasound pulses are transmitted from the transducer element 4 toward an intracorporeal portion of interest to receive return echoes. A radial ultrasound image can be obtained on the basis of these return echoes and output signals from the encoder 26 indicative of the rotational angle of the transducer element 4. In this connection, a rotation blocking member 27 is attached to the protective sleeve 7 in order to prevent the sleeve 2a and protective sleeve 7, which are fitted around the rotation transmitting member 2b, from being twisted upon turning the rotation transmitting member 2b. This rotation blocking member 27 is detachably fixed to a guide sleeve 11a which is provided on the casing 11 for guiding an operating rod 30 as will be described hereinlater.

The operating unit 10 further includes a linear scan mechanism for pulling the flexible cable 2 back and forth to scan the ultrasound transducer element 4 linearly over a predetermined range. The linear scan mechanism includes an operating rod 30 which serves as a probe operating means and which is mounted on the casing 11 slidably in the axial direction. The operating rod 30 is provided with a finger holder ring 30a at its outer end which is protruded out of the guide sleeve 11a on the casing 11. Extended sideward from a protruded end portion of the operating rod 30 is a connecting member 31 which releasably grips a proximal end portion of the flexible cable 2 covered with the protective tube 7 and threaded through the holes 8a and 12a in the mount piece 8 and mount portion 12. The flexible cable 2 is looped over a certain length between the point where it is gripped by the connecting member 13 and the connector 6 at its proximal end which is disengageably coupled with the operating unit 10.

After fixing the connecting member 31 to a proximal end portion of the flexible cable 2, if the operating rod 30 is pushed in and out with a finger on the finger holder 31, the rigid tip end portion 3 is moved back and forth together with the flexible cable 2 through the connecting member 31. Consequently, the ultrasound transducer element 4 on the rigid tip end portion 3 can be linearly displaced over a predetermined range. This linear displacement of the ultrasound transducer element 4 is detected by a linear position sensor mechanism which is provided in the casing 11. The linear position sensor mechanism includes a rack 32 which is formed on an inner surface of the casing 11, a pinion 33 in meshing engagement with the rack 32, and an encoder 34 coupled with a rotational shaft 33a of the pinion 33. The output signal of the encoder 34, which is indicative of the position of the operating rod 30, is fed to the ultrasound image observation terminal T as a position signal.

The operating rod 30 is constantly urged outward by a return spring 35 into a protruded position where a stopper 30b on the operating rod 30 is abutted against a guide member 36, which is provided within the casing 11, and can be pushed into the casing 11 against the biasing force of the return spring 35. An optical sensor 37 is located at the inward stroke end of the operating rod 30 to detect its location at the inward stroke end in cooperation with a light blocking plate 30c which is fixed on the inner end of the operating rod 30. Thus, the linear scan range of the ultrasound transducer element 4 corresponds to the stroke range of the operating rod 30 between the inner end position where the optical sensor 37 is intercepted by the light-blocking plate 30c and the outer position where the stopper 30b is abutted against the guide member 36. The inner stroke end position which is detected by the optical sensor 37 is taken as a reference position in determining an end position of the ultrasound image to be displayed on the monitor M. The reference position signal from the optical sensor 37 and the output signal of the encoder 34 are transferred to the ultrasound image observation terminal T through wires 37a and 34a in the cable 18.

Figure 5:
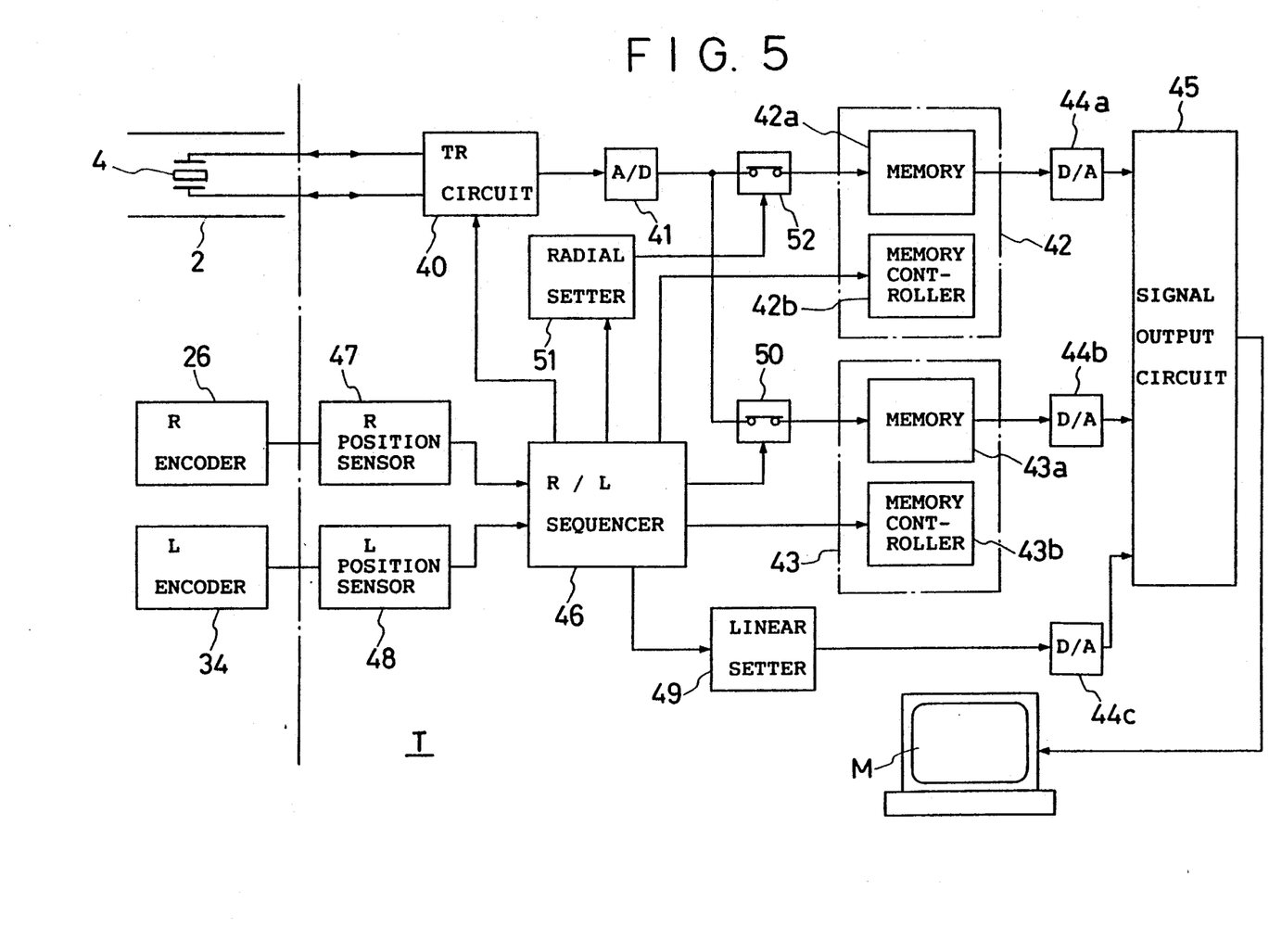
FIG. 5 is a circuit diagram of an ultrasound signal processor.

The ultrasound examination system is capable of producing ultrasound tomographic picture images in two perpendicularly intersecting directions, namely, radial ultrasound images and linear ultrasound images. More specifically, as seen in FIG. 5, the ultrasound transducer elements 4 is driven to transmit ultrasound pulses toward an intracorporeal portion of interest and receive the reflected return echoes, by signals from a transmission/reception (TR) circuit 40. The received echo signals are converted into digital signals through A/D converter 41, and stored in memory 42a of a radial scan converter 42 and also in memory 43a of a linear scan converter 43. Each time one frame of ultrasound picture data are fed to the radial and linear scan converters 42 and 43, these data are forwarded from the respective scan converters and converted into analog signals through D/A converters 44a and 44b, respectively. The resulting analog signals are transferred to the monitor M through a signal output circuit 45 to display side by side thereon bi-plane picture images of two perpendicularly intersecting directions, namely, a radial ultrasound picture image RP and a linear ultrasound picture image.

The signal processor is further provided with a radial/linear sequencer 46 for the purpose of controlling the ultrasound pulse transmission/reception by the TR circuit 40 and at the same time for the purpose of supplying control signals to memory controllers 42b and 43 which control the memories 42a and 43a of the radial and linear scan converters 42 and 43, respectively. This radial/linear sequencer 46 is supplied with a radial angle signal from a radial angle detector circuit 47 which detects the position in the radial direction of the ultrasound transducer element 4 on the basis of signals from the encoder 26, and also with a linear position signal from a linear position detector circuit 48 which detects the position in the linear direction of the ultrasound transducer element 4 on the basis of signals from the encoder 34. Further, a linear scan direction setter 49 is connected to the radial/linear sequencer 46. The linear scan direction setter 49 serves to specify the scanning direction of the linear ultrasound picture image LP to be displayed on the monitor M. For example, for this purpose, a volume (not shown) may be provided on the operating unit 10, so that the operator can manually enter a signal as to which one of the lines of radial directions should be sampled for the linear ultrasound picture image. According to the signal of a specified linear scan direction, which is received from the linear scan direction setter 49, the radial/linear sequencer 46 operates a switch which is inserted in a stage anterior to the memory 43a of the linear scan converter 43, thereby selectively sampling the signals in the specified angular position alone. Further, a radial range setter 51 is connected to the radial/linear sequencer 46. This radial range setter 51 serves to delimit the sampling angle of the radial ultrasound picture image RP to a particular range of interest. According to a sampling angle or direction specified through the radial range setter 51, the radial/linear sequencer 46 operates a switch 52 which is inserted in a stage anterior to the memory 42a of the radial scan converter 42 to supply the memory 42a with return signals in the specified angular range alone.

Figure 6:
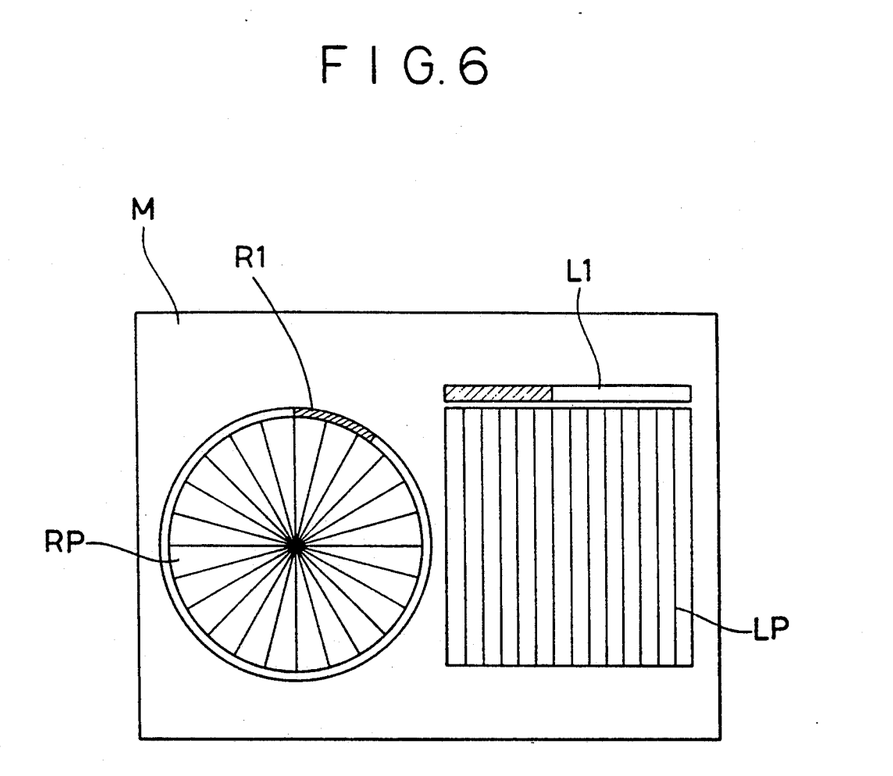
FIG. 6 is a diagrammatic view of a display mode on a monitor screen.

As described above, a radial ultrasound picture image RP and a linear ultrasound picture image LP are simultaneously displayed on the monitor M. The bi-plane picture image consisting of the radial and linear ultrasound images RP and L is displayed together with radial and linear indicators RI and LI, respectively. The radial indicator RI which is associated with a radial ultrasound picture image RP indicates the direction or angular position of the radial ultrasound picture image which is currently on display, while the linear indicator LI which is associated with a linear ultrasound picture image LP indicates the position of the ultrasound transducer element 4, namely, the position of the displayed radial ultrasound picture image RP in the linear direction. The directional or positional signs of the radial and linear indicators RI and LI are obtained by detecting the direction and position of the ultrasound transducer element 4 by the radial/linear sequencer 46 on the basis of signals from the linear direction setter 49 and linear position sensor circuit 48 and supplying the resulting directional and positional signals to the signal output circuit 45 through D/A converter 44c to combine them with the radial and linear ultrasound picture images, showing the directional and positional signs preferably in a graphically depicted form in association with the corresponding ultrasound picture image.

The above-described radial scan type ultrasound internal examination system operates in the manner as follows.

Firstly, the endoscope S is inserted into the patient's body until its tip end reaches an intracorporeal portion to be examined for diagnostic or other purposes. Then, the flexible cable 2 of the ultrasound probe 1 is inserted into a biopsy channel C of the endoscope S, letting the rigid portion 3 at the tip end of the flexible cable 2 protrude from the fore end of the biopsy channel C over a predetermined length, and then the mount portion 12 on the casing 11 of the operating unit 10 is fixedly joined to the entrance opening CE of the biopsy channel C through the mount piece 8. Then, before or after fixing the connecting member 31 to a proximal end portion of the flexible cable 2, the connector 6 at the terminal end of the flexible cable 2 is coupled with the connector 13 on the operating unit 10. Thereafter, the motor 25 is actuated to put the rotary member 14 in rotation, which rotation is transmitted to the ultrasound transducer element 4 through the rotation transmitting member 2b. In this state, if the operating rod 30 is pushed in fully to the end position of its inward stroke, the turning ultrasound transducer element 4 is displaced to a position corresponding to an initial point of its linear stroke. At this point, the location of the ultrasound transducer element 4 at the inner stroke end position is detected by the optical sensor 37 in cooperation with the light blocking plate 30c. This position is taken as an initial position of linear scan by the ultrasound transducer element 4.

If the ultrasound probe 1 is pulled back in this state, the echo signals which are received by the ultrasound transducer element 4 during this outward stroke are sequentially transferred to the TR circuit 40. Unless the sampling angle is delimited by the radial range setter 49, all of the received echo signals are forwarded to the memory 42a of the radial scan converter 42, and ultrasound tomographic images are sequentially displayed on the monitor M as a radial ultrasound picture image RP one after another in step with the revolution of the ultrasound transducer element 4. On the other hand, of the acoustic lines which constitute the radial ultrasound picture image, the echo signals from the direction specified by the linear direction setter 47 are sequentially fed to the memory 43a of the linear scan converter 43 from the TR circuit 40. Accordingly, on the basis of the output signals of the linear scan converter 43, a linear ultrasound picture image LP and a radial ultrasound picture image RP are displayed on the monitor M in the bi-plane mode. The simultaneous display of ultrasound tomographic images of two perpendicularly intersecting directions makes it possible to grasp the condition of intracavitary wall tissues three-dimensionally when checking or identifying a disease. Of the two displayed ultrasound picture images, the radial ultrasound image RP is totally renewed on every revolution of the ultrasound transducer element 4 and therefore is displayed as a motion picture, while the linear ultrasound image LP is displayed as a still picture which is incrementally added with a new section of picture image as the ultrasound transducer element 4 comes to a next phase of linear scan by a displacement in the axial direction.

In the above-described ultrasound scanning operation, should there be spotted a doubtful portion which needs a closer examination, the operator can easily confirm the position of such doubtful portion with reference to the indicators LI and RI. In such a case, it is preferable to obtain the radial and linear ultrasound images in the entire scan range by once moving the ultrasound transducer element 4 fully from end to end of its stroke, and, for closer examination, to relocate the ultrasound transducer element 4 in a position confronting the doubtful portion with reference to the directional and positional signs on the radial and linear indicators RI and LI. The doubtful portion can be examined in a concentrated manner by narrowing the scanning pitch of the ultrasound transducer element 4. Besides, while reciprocating the ultrasound transducer element 4 in a range of particular interest, the linear direction setter 47 may be operated to change the sampling direction in each reciprocating movement to obtain linear ultrasound images of a particular locality in sequentially shifted angular positions along with a radial ultrasound image which is renewed at predetermined time intervals. This permits to grasp the condition of a diseased portion three-dimensionally, and provides necessary data for synthesizing a three-dimensional image of the diseased portion by suitable three-dimensional signal processing.

In some cases, instead of simultaneously obtaining radial and linear ultrasound images, one may only need to spot a location in the linear direction in connection with a radial ultrasound image obtained by the radial scanning or to spot a location in the radial direction in connection with a linear ultrasound image obtained by the linear scanning. For example, it is possible to build up a three-dimensional image of a diseased portion if one can obtain radial ultrasound images which are sampled correctly and uniformly at intervals of a predetermined pitch width. Alternatively, a three-dimensional image of a diseased portion can be built up on the basis of linear ultrasound images which are sampled at a plural number of angularly shifted positions.

Figure 7:
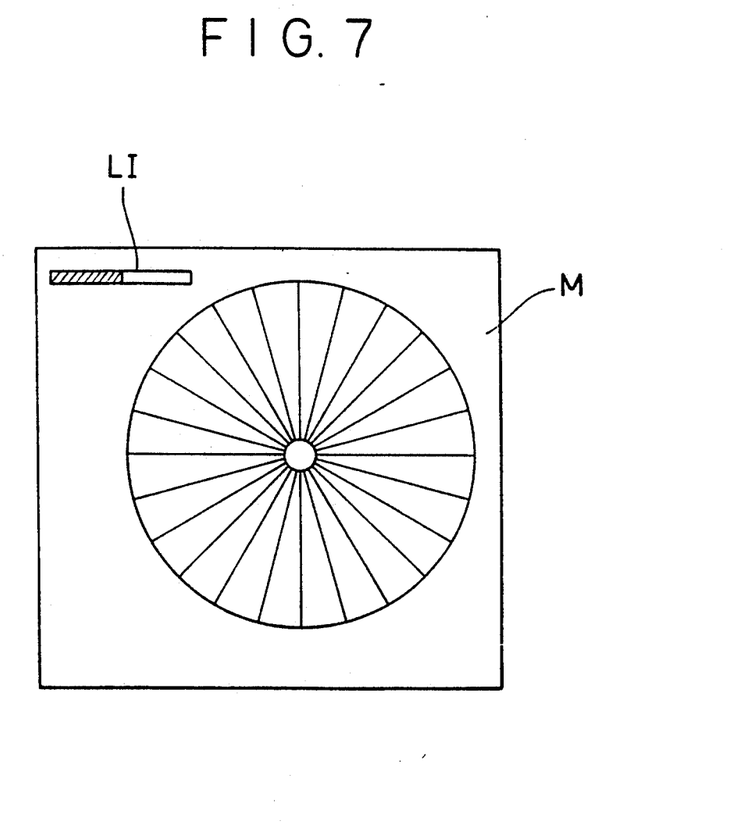
FIG. 7 is a diagrammatic view of another display mode in a modified second embodiment of the invention.
Figure 8:
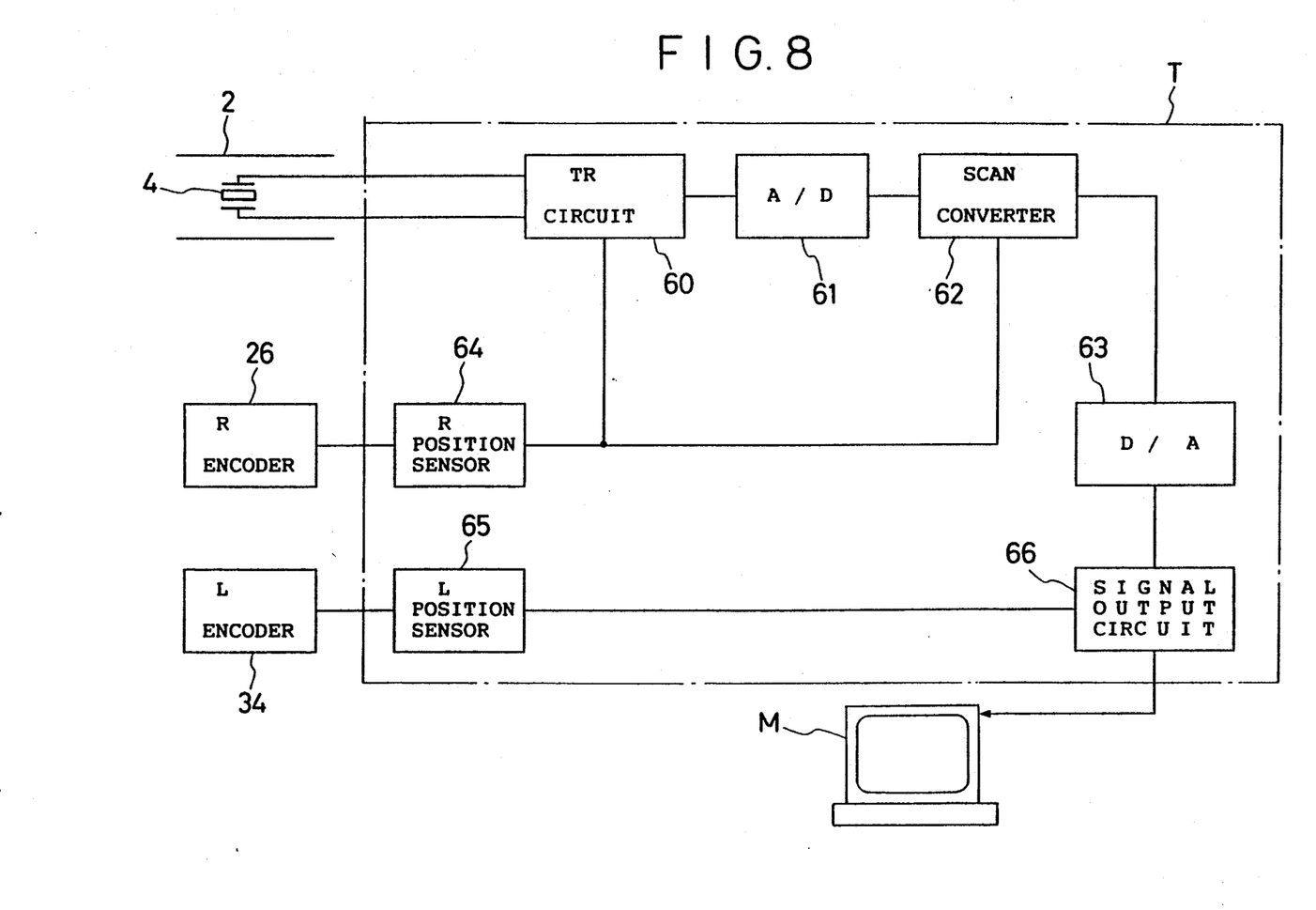
FIG. 8 is a circuit diagram of an ultrasound signal processor for the display mode of FIG. 7.

For these reasons, arrangements may be made to display a radial ultrasound image RP along with a linear indicator LI as shown in FIG. 7. To this end, the signal processor of the ultrasound image observation terminal T may employ a circuitry as shown in FIG. 8.

More specifically, the echo signals of ultrasound pulses, which are transmitted into an intracavitary portion from the ultrasound transducer element 4 according to signals from TR circuit 60, are converted into digital signals through A/D converter 61 and stored in the memory of a scan converter 62. This scan converter 62 corresponds to the radial scan converter 42 in the above-described first embodiment of the invention, but this circuitry does not include components corresponding to the linear scan converter 43 and radial/linear sequencer 46. As soon as one frame of data is fed to the scan converter 61, these ultrasound picture data are read out from the scan converter 61 and converted into analog signals through D/A converter 63 to display an ultrasound picture image on the monitor M. The ultrasound pulse is shot off at predetermined angular intervals in each revolution of the ultrasound transducer element 4. For the purpose of setting the timing for the ultrasound pulses shooting and at the same time for the purpose of setting the display positions of reflected echo signals on the monitor M, a position signal indicative of the rotational angular position of the ultrasound transducer element 4 is supplied to a radial position detector circuit 64 from the radial encoder 26. The output signal of the radial position detector circuit 64 is supplied to TR circuit 60 and scan converter 62.

Accordingly, in this instance, as the operating rod 30 on the operating unit 10 is manipulated to shift the position of the ultrasound transducer element 4 linearly, the location of the transducer element 4 is constantly monitored by the linear encoder 34. The output signal of the linear encoder 34 is supplied to a linear position detector circuit 65, and the resulting data on the linear position are combined with the data of a radial ultrasound picture image at a signal output circuit 66 to display the linear position as a linear indicator LI on the monitor M along with the ultrasound picture image.

Figure 9:
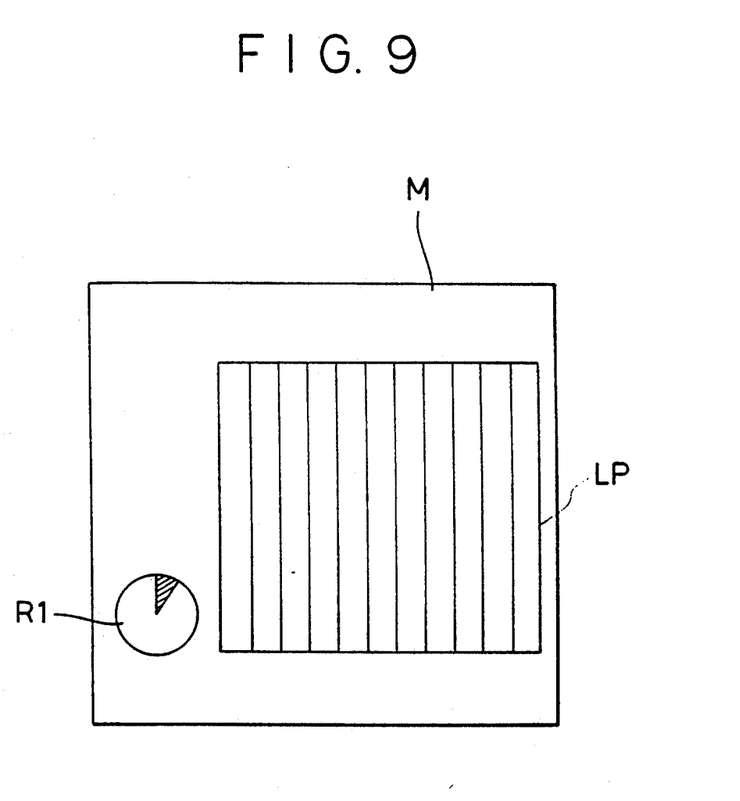
FIG. 9 is a diagrammatic view of a display mode on a monitor screen in another modified third embodiment of the invention.
Figure 10:
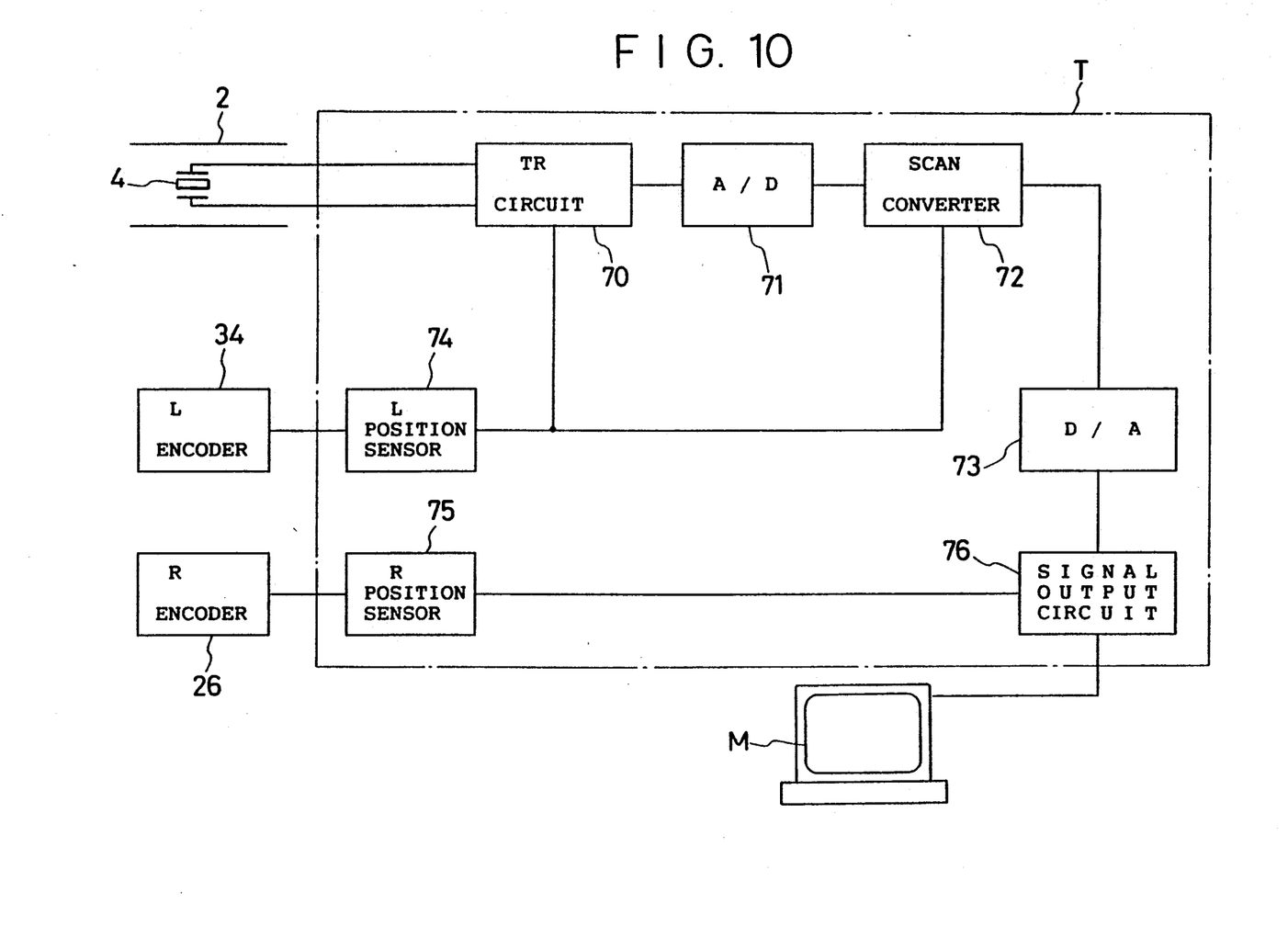
FIG. 10 is a circuit diagram of an ultrasound signal processor for the display mode of FIG. 8.

Referring now to FIG. 9, there is shown another embodiment employing a modified display mode, in which a linear ultrasound picture image LP resulting from linear scanning of the ultrasound transducer element 4 is displayed on the monitor M along with a radial indicator RI which indicates the angular direction of the linear scanning. For this display mode, the signal processor of the ultrasound image observation terminal T is preferably arranged as shown in FIG. 10. In this case, there is no need for providing the electric motor 25 or a similar drive means for turning the ultrasound transducer element 4 in the radial direction. However, in order to permit the operator to turn the ultrasound transducer element 4 manually, it is necessary to provide the rotary member 14 and the rotary connector 15 as rotating means. In this case, the coupling socket 6b of the connector 6 is fitted on the rotary member 14 in such a way that the operator can manually turn the coupling socket 6b to rotate the ultrasound transducer element 4 to a desired direction.

As shown in FIG. 10, drive signals are applied to the ultrasound transducer element 4 from a TR circuit 70 in the same manner as in the foregoing embodiments, and the return echo signals received by the TR circuit 70 are converted into digital signals through A/D converter 72 and damped into the memory of a scan converter 72. The scan converter 72 corresponds to the scan converter 43 of the first embodiment, but this circuitry does not include the radial scan converter 42 and radial/linear sequencer 46. Each time one frame of ultrasound image data are fed to the scan converter 72, these data are read out from the scan converter 72 and converted into analog signals through D/A converter 73 to display a linear ultrasound picture image LP on the monitor M. In this instance, for the purpose of setting the timing of ultrasound pulse transmission by the TR circuit 70 and at the same time for the purpose of setting the ultrasound image display position on the monitor M, the output signal of the linear encoder 34 is fed to the linear position detector circuit 74, the output signal of which detector circuit 74 being applied to the TR circuit 70 as a transmission trigger signal and also to the scan converter 72 as an address signal for the image display.

Further, the position in the radial direction of the ultrasound transducer element 4 is displayed on the monitor M by the use of the output signal of the radial encoder 26, which is indicative of the rotational angular position of the ultrasound transducer element 4. The output signal of the radial encoder 26 is applied to the radial position detector circuit 75 thereby to determine the position of the ultrasound transducer element 4 in the radial direction. This signal of the radial position of the ultrasound transducer element 4 is forwarded to the signal output circuit 76 and combined with the linear ultrasound image signal which is concurrently transferred to the signal output circuit 76 through D/A converter 73, to display on the monitor M a linear ultrasound picture image along with a radial indicator RI giving the data on the radial or angular position of the ultrasound transducer element 4.

In this manner, according to the above-described second and third embodiments, the axial position or the radial or angular direction of the ultrasound transducer element 4 is displayed by the linear or radial indicator LI or RI along with a radial or linear ultrasound picture image while scanning the transducer element 4 in the radial or linear direction, so that the operator can immediately recognize the current position or direction of the transducer element 4 on the screen. This is very convenient because, after taking a radial or linear ultrasound tomographic image, the ultrasound transducer element 4 can be quickly relocated in a next position of examination. In case a tumor or a diseased portion is spotted by the ultrasound scanning by the transducer element 4, there may arise a necessity for scanning the diseased portion in a more concentrated manner and with a finer scanning pitch for closer examination. In such a case, the position or direction of the ultrasound transducer element 4 can be varied accurately with reference to the linear indicator LI or radial indicator RI to obtain ultrasound picture images with accuracy which is required in a closer examination of the diseased portion. Besides, when the ultrasound transducer element 4 is largely displaced from one position to another for successive scanning operations at two different positions, it can be easily relocated in the first position easily in an accurate manner. Furthermore, the records of the ultrasound examinations, which contain the positional or directional information along with the ultrasound picture images, also contribute to improve the quality of examinations. In case a plural number of ultrasound tomographic images are sampled at certain angular intervals, it becomes possible to synthesize a three-dimensional image of a diseased portion or the like from the sampled data after suitable three-dimensional image processing.

Figure 11:
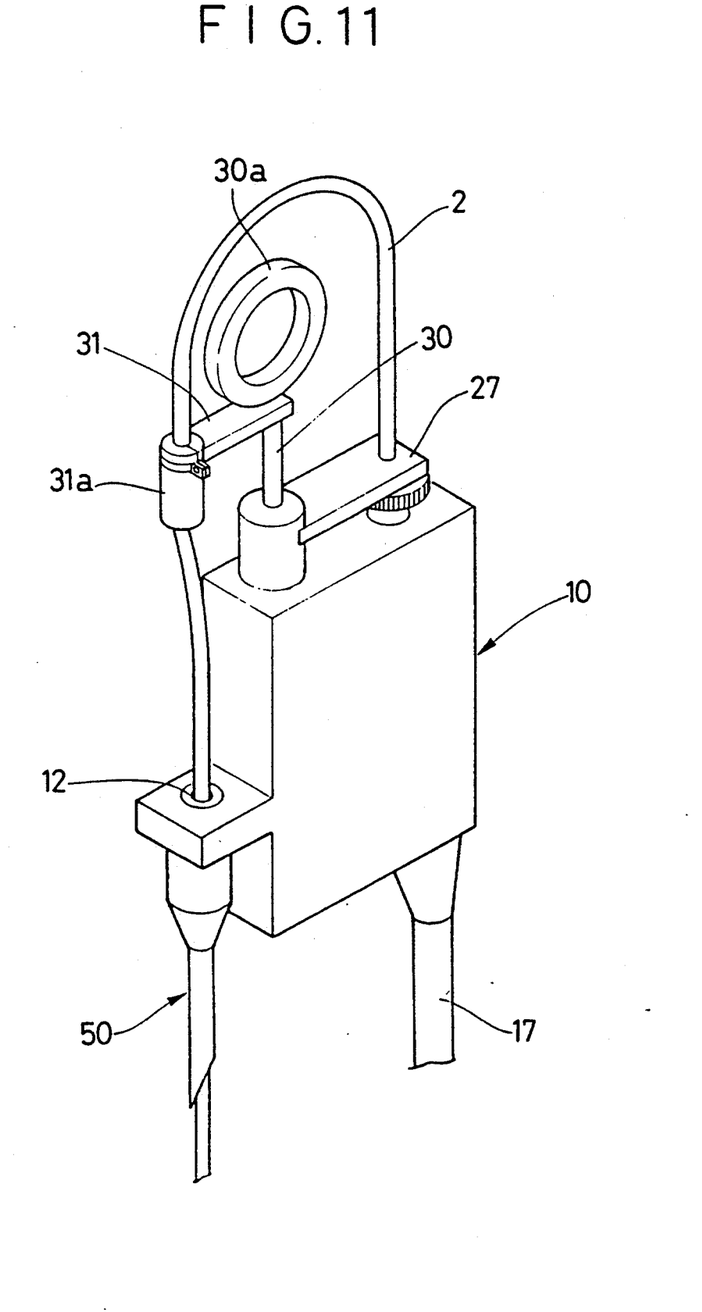
FIG. 11 is a schematic outer view of an operating unit in a further embodiment of the invention.
Figure 12:
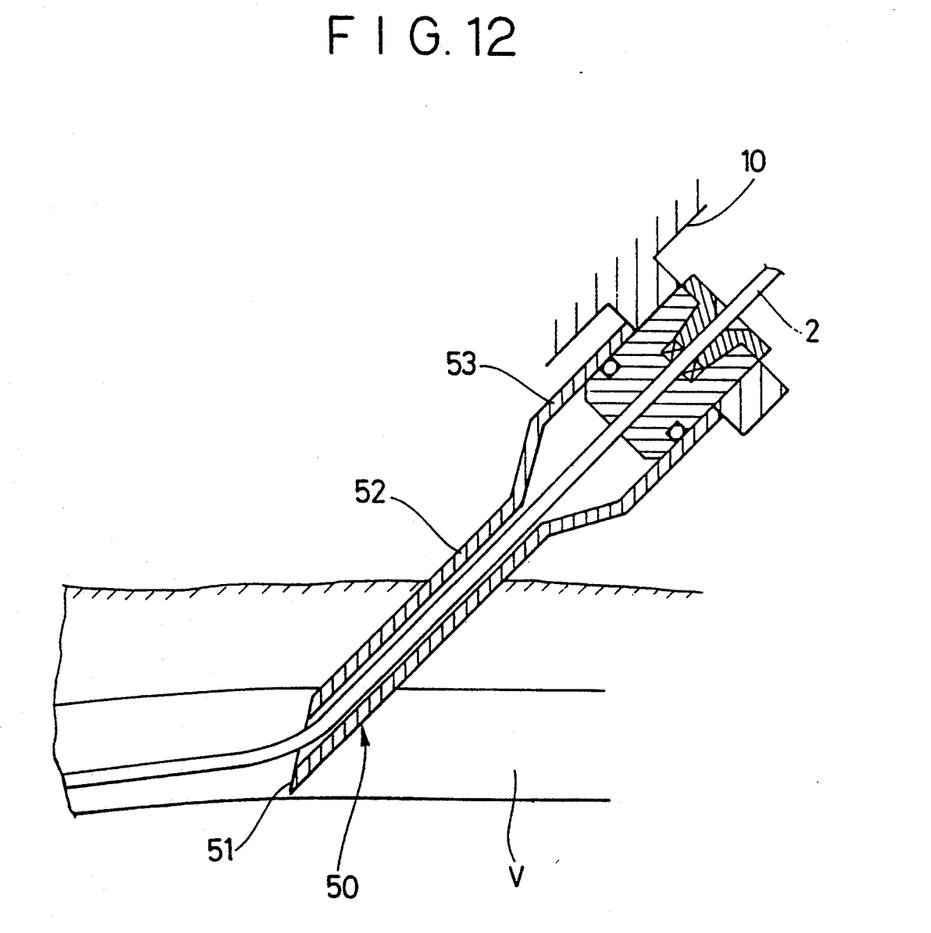
FIG. 12 is a schematic view explanatory of the arrangement of a trocar.

Referring to FIGS. 11 and 12, there is shown a fourth embodiment of the invention, employing an ultrasound probe 1 which is arranged to be inserted into a blood vessel. In case of a blood vessel type fine probe of this sort, which cannot be inserted by the use of an endoscope, a blood vessel V itself is utilized as a guide for the ultrasound probe 1. In this case, a trocar 80 is employed for the purpose of introducing the ultrasound probe 1 into the blood vessel V. As seen in FIG. 12, the trocar 80 is provided with a mount portion 83 of a larger diameter at the proximal end of a cylindrical body 80 to be attached to the operating unit 10, and sharp-pointed at its fore end for piercing the blood vessel wall. The ultrasound probe 1 and operating unit 10 are arranged substantially in the same manner as in the above-described first embodiment, and therefore the description and illustration of details of these components are omitted here to avoid unnecessary repetitions.

With the above-described arrangement, radial and linear ultrasound data of tissues of the blood vessel V can be simultaneously sampled along the length thereof, and displayed on the monitor M as a bi-plane ultrasound picture image, permitting the operator to grasp the condition of a particular locality under examination three-dimensionally and accurately, for example, when checking for the position or the degree of obliteration of the blood vessel V.

What is claimed is:

1. An ultrasound internal examination system, comprising:

an ultrasound probe to be inserted into an internal portion of interest by one of direct insertion and insertion through a guide means, said ultrasound probe having a rotatable single-element ultrasound transducer mounted at the tip end of a flexible cable with drive means to move said transducer back and forth in a linear direction for a linear scan in a predetermined range while permitting said transducer to rotate for a radial scan at an arbitrary position in the linear direction;

a probe operating unit operatively coupled with said ultrasound probe and equipped with remote control means for said ultrasound transducer, including a rotating means, a linearly reciprocating means, an angular position sensor means, and a linear position sensor means;

a signal processing means operatively connected to said ultrasound transducer and said angular and linear position sensors, and adapted to produce at least an ultrasound tomographic image of one of radial and linear scan directions on the basis of ultrasound echo signals from said ultrasound transducer and signals from said angular and linear position sensor means and to hold at least a signal of one of the linear and angular position of said ultrasound transducer in the other scan direction; and a monitor arranged to display at least said ultrasound tomographic image of one of radial and linear scan directions on a monitor screen along with at least an indicator giving a sign of one of linear and angular position of said ultrasound transducer according to signals from said signal processing means.

2. An ultrasound internal examination system as defined in claim 1, further comprising guide means including a biopsy channel of an endoscope, and wherein said probe operating unit is adapted to be detachably mounted on a proximal end portion of said biopsy channel.

3. An ultrasound internal examination system as defined in claim 1, wherein said signal processing means is adapted to produce ultrasound tomographic images of radial and linear scan directions on the basis of ultrasound echo signals from said ultrasound transducer, and to hold signals of linear and angular positions of said ultrasound transducer, and said monitor is arranged to display said tomographic ultrasound images of radial and linear scan directions on said monitor screen according to singals from said signal processing means, along with indicators showing linear and angular positions of said ultrasound transducer.

4. An ultrasound internal examination system as defined in claim 1, wherein said signal processing means is adapted to produce a radial tomographic ultrasound image on the basis of ultrasound echo signals from said ultrasound transducer in a radial scan and to hold a signal of the position in the linear direction of said ultrasound transducer in relation with said radial scan, and said monitor is arranged to display said radial ultrasound image on said monitor screen according to signals from said signal processing means, along with an indicator showing the linear position of said radial ultrasound image.

5. An ultrasound internal examination system as defined in claim 1, wherein said signal processing means is adapted to produce a linear tomographic ultrasound image on the basis of ultrasound echo signals from said ultrasound transducer in a linear scan and to hold a signal of the angular position of said ultrasound transducer in relation with said linear scan, and said monitor is arranged to display said linear ultrasound image on said monitor screen according to signals from said signal processing means, along with an indicator showing the angular position of said linear ultrasound image.

* * * * *